US008940674B2

(12) United States Patent
Fernandez de Castro et al.

(10) Patent No.: US 8,940,674 B2
(45) Date of Patent: Jan. 27, 2015

(54) HIGH ALCOHOL CONTENT FOAMING COMPOSITIONS

(71) Applicant: Deb Worldwide Healthcare Inc., Brantford (CA)

(72) Inventors: Maria Teresa Fernandez de Castro, Brantford (CA); Bruce Michael Koivisto, Willsonville (CA)

(73) Assignee: Deb Worldwide Healthcare Inc., Brantford (CA)

( * ) Notice: Subject to any disclaimer, the term of this patent is extended or adjusted under 35 U.S.C. 154(b) by 0 days.

(21) Appl. No.: 14/065,246

(22) Filed: Oct. 28, 2013

(65) Prior Publication Data
US 2014/0094437 A1   Apr. 3, 2014

Related U.S. Application Data

(60) Continuation of application No. 13/479,630, filed on May 24, 2012, now Pat. No. 8,569,219, which is a continuation of application No. 12/659,063, filed on Feb. 24, 2010, now abandoned, which is a division of application No. 11/507,626, filed on Aug. 22, 2006, now Pat. No. 7,683,018, which is a continuation of application No. 10/952,474, filed on Sep. 29, 2004, now Pat. No. 7,199,090.

(60) Provisional application No. 60/591,601, filed on Jul. 28, 2004, provisional application No. 60/506,172, filed on Sep. 29, 2003.

(51) Int. Cl.
| C11D 3/43 | (2006.01) |
|---|---|
| C11D 3/24 | (2006.01) |
| A61K 31/661 | (2006.01) |
| A01N 31/02 | (2006.01) |
| A61K 8/04 | (2006.01) |
| A61K 8/34 | (2006.01) |
| A61K 8/81 | (2006.01) |
| A61K 8/86 | (2006.01) |
| A61L 2/235 | (2006.01) |
| A61Q 17/00 | (2006.01) |
| A61Q 19/00 | (2006.01) |
| C11D 1/00 | (2006.01) |
| C11D 3/00 | (2006.01) |
| C11D 3/20 | (2006.01) |
| C11D 17/00 | (2006.01) |
| A61K 31/045 | (2006.01) |
| A61K 31/08 | (2006.01) |
| A61K 31/195 | (2006.01) |
| A61K 45/06 | (2006.01) |

(52) U.S. Cl.
CPC .......... *A61K 31/661* (2013.01); *A01N 31/02* (2013.01); *A61K 8/046* (2013.01); *A61K 8/34* (2013.01); *A61K 8/8123* (2013.01); *A61K 8/86* (2013.01); *A61L 2/235* (2013.01); *A61Q 17/005* (2013.01); *A61Q 19/00* (2013.01); *C11D 1/004* (2013.01); *C11D 3/0094* (2013.01); *C11D 3/201* (2013.01); *C11D 3/2013* (2013.01); *C11D 17/003* (2013.01); *A61K 31/045* (2013.01); *A61K 31/08* (2013.01); *A61K 31/195* (2013.01); *A61K 45/06* (2013.01)
USPC .......... 510/138; 510/130; 510/149; 510/157; 510/432; 510/436

(58) Field of Classification Search
USPC ................. 510/130, 138, 149, 157, 432, 436
See application file for complete search history.

(56) References Cited

U.S. PATENT DOCUMENTS

| 2,054,989 | A | 9/1936 | Moore |
|---|---|---|---|
| 3,131,153 | A | 4/1964 | Kenneth |
| 3,962,150 | A | 6/1976 | Viola |
| 4,440,653 | A * | 4/1984 | Briscoe et al. ............. 507/202 |
| 4,956,170 | A | 9/1990 | Lee |
| 5,167,950 | A | 12/1992 | Lins |
| 5,629,006 | A | 5/1997 | Hoang et al. |
| 5,906,808 | A | 5/1999 | Osborne et al. |
| 5,928,993 | A | 7/1999 | Johansson |
| 6,090,395 | A | 7/2000 | Asmus et al. |
| 6,117,440 | A * | 9/2000 | Suh et al. ................. 424/407 |
| 6,423,329 | B1 * | 7/2002 | Sine et al. ................. 424/405 |
| 6,623,744 | B2 | 9/2003 | Asmus et al. |
| 2002/0098159 | A1 * | 7/2002 | Wei et al. ................. 424/70.1 |

* cited by examiner

*Primary Examiner* — Charles Boyer
(74) *Attorney, Agent, or Firm* — Neal, Gerber & Eisenberg LLP

(57) ABSTRACT

This invention relates to a "high lower alcohol content" (>40% v/v of a $C_{1-4}$ alcohol) liquid composition able to be either dispensed as a stable foam with the use of non-propellant foam dispensing devices from non-pressurized containers or as an alcohol gel composition which does not use thickener and gelling agents that leave undesirable deposits or a sticky after-feel and that has a final viscosity less than 4,000 cps. The liquid compositions comprise an alcohol, $C_{1-4}$ (>40% v/v), a fluorosurfactant of at least 0.001% by weight to prepare a foamable composition or from 0-2.0% to prepare a gel-like composition of a final viscosity less than 4,000 cps, 0-10% w/w of additional minor components added to obtain the desired performance (a foamable composition or a gel-like composition with a viscosity less than 4,000 cps), and the balance being purified water.

20 Claims, No Drawings

HIGH ALCOHOL CONTENT FOAMING COMPOSITIONS

CROSS REFERENCE TO RELATED U.S. APPLICATIONS

This patent application is a continuation of U.S. application Ser. No. 13/479,630, filed on May 24, 2012 and which is pending, which is a continuation of U.S. application Ser. No. 12/659,063, filed on Feb. 24, 2010 and which is abandoned, which is a division of U.S. application Ser. No. 11/507,626, filed on Aug. 22, 2006 and which issued as U.S. Pat. No. 7,683,018, which is a continuation of U.S. application Ser. No. 10/952,474, filed on Sep. 29, 2004 and which issued as U.S. Pat. No. 7,199,090, which further claims the priority benefit from U.S. Provisional Application No. 60/591,601, filed on Jul. 28, 2004, and from U.S. Provisional Application No. 60/506,172, filed on Sep. 29, 2003, with all the foregoing applications being incorporated herein by reference in their entireties.

FIELD OF THE INVENTION

The present invention relates to compositions with high contents of lower alcohol ($C_{1-4}$) that could be a gel-like composition or a solution able to be dispensed as a foam. The compositions to be dispensed as foams contain a fluorosurfactant and when mixed with air provide a stable alcohol foam which can be used for personal cleaning or for disinfecting purposes. The gel-like compositions may or may not contain a fluorosurfactant.

BACKGROUND ART

Ethanol and/or Isopropyl alcohol compositions with at least 60% percent v/v (approximately 52% by weight) are well known to be antibacterial, therefore widely accepted for disinfecting purposes. Nonetheless due to the inherent characteristics of alcohol, it is perceived that the higher the content the better the product and a higher than 60% by volume alcohol content solution is more desirable.

Alcohol disinfectant solutions are generally thickened in order to eliminate the waste and facilitate spreading the composition throughout the desired area. It is also known that other than gelling agents one can use paraffin or waxes to achieve thickening of a solution with high alcohol concentration. Such a composition added with lanolin to reduce the melting point closer to body temperature is described in U.S. Pat. No. 2,054,989. One of the disadvantages of gels and such type thick alcohol containing compositions is that if they do not leave a tacky feeling on the hands after one use (although some do), the effect builds up after repetitive use during the day, making it necessary to eventually wash off the thickeners before continuing the usage of an alcohol antiseptic solution. The present invention if formulated for such type of product does not leave such a feel, and does not need to be washed off after having been used repeatedly.

Another way of thickening high alcohol content solutions has also been taught in U.S. Pat. Nos. 6,090,395 and 6,623,744 where they use emulsifiers and surfactants as the thickening system to produce a hydroalcoholic lotion with a viscosity of at least 4,000 cps. Also, U.S. Pat. No. 4,956,170 discloses polyethoxylated non-ionic surfactants/emulsifiers to stabilize the added emollient oils in addition to a fatty alcohol although with the addition of a polymeric thickening agent to prepare a hydroalcoholic skin moisturizing/conditioning antimicrobial gel. The disinfecting compositions of the present invention that are gel-like have a viscosity lower than 4,000 cps and no polymeric thickening agent is added.

Generally speaking a high alcohol content disinfectant solution disinfects but does not clean. In order to make them disinfect and clean, so much soap would be needed that the skin would feel soapy and disagreeable, unacceptable for rubbing alcohol purposes. Nonetheless, a non-irritant skin disinfecting high lower alcohol content formulation for use as a skin-washing agent is successfully attained by combining emulsifiers, surfactants and skin emollients to be used as a gel or ointment as described in U.S. Pat. No. 5,629,006.

Surfactants other than for cleaning purposes are also used for spreading an aqueous composition containing one or more active substances rapidly and evenly over a surface due to their wetting properties. The use of good wetting agents definitely improves the efficient use of active substances in different compositions as described in U.S. Pat. No. 5,928,993. Hence, the composition described in the present invention includes the addition of surfactants, specifically fluorosurfactants which are well known for their unparalleled wetting power and which are also surface-active in the lower alcohols used as disinfectant and solvent system in levels which make it acceptable even for rubbing alcohol purposes, providing cleaning, wetting and foaming properties to the composition.

Although a high alcohol content disinfectant solution has good disinfectant characteristics, it has a sharp smell and is generally perceived to cause drying of the skin, characteristics which can also be diminished to a desirable level in the present invention.

A greater than 40% v/v alcohol foam product, easy and safe to use, is desirable over conventional gel or ointment type composition products. The concentration of alcohol already poses a hazard in itself, and there are many applications in which the perceived risk may be diminished if it could be dispensed as a foam without the use of pressurized aerosol containers. A foam intended to be useful as a skin disinfecting agent must have a uniform consistency, spreadability, cleansing ability, and have a pleasant feel, i.e. have rapid breaking power when pressure is applied; all of which present a challenge for a high lower alcohol content composition.

The description of an aqueous foaming skin disinfecting composition using 15% w/w alcohol as a co-solvent, which requires no pressurized container or added propellant to produce the foam, is described in U.S. Pat. No. 3,962,150.

The foam-forming agents utilized heretofore, have been incapable of forming stable foams when the liquid phase has high alcohol content without using other ingredients. Furthermore, lower alcohols have been considered to be defoamers rather than foam-promoting chemicals. According to Klausner, in U.S. Pat. No. 3,131,153, if more than 64% alcohol is used non-homogeneous compositions are obtained. The compositions in the patent required propellant to foam and the foams produced were of limited stability.

Prior to this invention, when a greater than 40% v/v alcohol concentration is required in a product, it is generally accepted that the product will be either liquid or gel, and that if a foam is desired then the concentration of alcohol would need to be reduced or the use of a propellant and a pressurized system would be required.

Surprisingly, in the few "foamable" high alcohol content products disclosed, the types of foam obtained were not similar to those expected from aqueous solutions. The foams obtained are described as fast or aerated foam, quick breaking, with low or limited stability, which would not last for more than one minute, being generally gone within seconds.

It has been disclosed that fluorosurfactants and alcohol can be combined to produce a "stable" foam by a process using high-pressurized means to generate the foam. Highly stable pressurized foams containing high lower alcohol contents and methods of forming and using such pressurized foams in the oil industry using a non-ionic surfactant or mixture of non-ionic surfactants of a specific group of fluorosurfactants are provided in U.S. Pat. No. 4,440,653. The compositions in this patent require the use of a pressurized gas system to generate the foam.

Various examples of compositions with a high lower alcohol content that are dispensed as a foam have been described, although for the purpose of the present invention the characteristics of the foam are not of the desired outcome, since they are fast breaking, of low stability and the foam is produced by means of propellants and aerosol containers only, as the one described in U.S. Pat. No. 5,906,808, which discloses a product that uses an emulsifying wax NF, and a combination of stearyl and cetyl alcohol, or other wax combinations, which improve the foaming performance of the composition, in combination with cetyl lactate, to produce a 0.8% chlorhexidine gluconate alcohol product.

U.S. Pat. No. 5,167,950 issued to Lins discloses a foam product which requires a propellant and no surfactant is added as a cleaning agent. The composition disclosed in this patent is based upon using an emulsifier system (fatty alcohol ROH 16-22 carbons) in combination with the use of a thickening agent (carbomer, klucel, etc.).

U.S. Pat. No. 5,167,950 to Lins discloses an antimicrobial aerosol mousse having a high alcohol content. The mousse comprises alcohol, water, a polymeric gelling agent and a surfactant system comprising a C16-C22 alcohol, aerosol propellant and a non-ionic polyethoxylated surfactant. Despite the work done to date it has been shown that there is little specific knowledge on how foams react and are formed, and surprisingly formulations that might seem not foamable result in the best foam producing ones while other formulations which seemed to have been producing foam even while being prepared did not perform well at all in some non-aerosol foam dispensers. The behaviour of aqueous foams is not the same of that of an alcohol foam.

The traditional ways of forming a gel using polymeric thickeners presents undesirable characteristics and similarly little has been done in forming emulsion-like thickened gels.

It would be very advantageous to have alcohol based disinfecting formulations which may be dispensed as either a gel or a foam. Further, it would be very advantageous and desirable to find a foaming agent that could be used in concentrations that would allow it to be used in products that can remain in the area on which they have been applied and do not need to be rinsed or wiped off due to small amounts of residue remaining after evaporation. Thus it would also be very advantageous to provide foams or gels that do not leave an unpleasant sticky after-feel as most commercial alcohol gel products are known to, or which clog up the dispensing equipment used to dispense the foams and gels.

SUMMARY OF THE INVENTION

It is an object of this invention to provide high alcohol content liquid compositions, which contain a surfactant/cleaning agent as well as a disinfectant/cleaning/solvent/carrier and that causes very little drying to the skin or the hands of the user and is able to be dispensed either as a gel or as a foam from both pressurized and non-pressurized systems.

The present invention provides high alcohol content compositions that are either gels or able to be dispensed as a foam, which are readily spread over the desired surface. Amongst the different applications where such compositions might be of use, it is another object to also provide an antimicrobial alcohol foam and an antimicrobial alcohol gel. The foamable compositions when dispensed from a suitable dispenser are stable and do not require the use of propellants and pressurized containers. The gels disclosed herein with a viscosity of less than 4,000 cps do not use the gelling or thickening agents typically used in commercial gels and therefore after single or multiple applications of the gel there is not the usual tacky or sticky after-feel and the gel does not clog the dispensers from which the gels are dispensed.

These and other objects and advantages will be apparent from the following description of the invention. All percentages provided herein are based on the total weight unless otherwise indicated.

Accordingly, the present invention provides compositions for personal hygiene, as follows.

Foamable Compositions

The present invention provides a foamable composition, comprising:

a) an alcohol $C_{1-4}$, or mixtures thereof, present in an amount greater than about 40% percent v/v of the total composition;

b) an effective fluorinated surface active agent for wetting and foaming present in an amount of at least 0.001% weight percent of the total composition; and c) water present in an amount to balance the total composition to 100% weight percent.

In this aspect of the invention the effective fluorinated surface active agent is present in an amount from about 0.001% to about 10.0% weight percent of the total composition which is physiologically acceptable so it can be used in personal care type products.

In a preferred embodiment of the invention the fluorosurfactant may be an amphoteric polytetrafluoroethylene acetoxypropyl betaine of the following formula, $(CF_3CF_2(CF_2CF_2)nCH_2CH_2(OAc)CH_2N+(CH_3)_2CH_2COO—)$ where n=2 to 4, an ethoxylated nonionic fluorosurfactant of the following structure: $RfCH_2CH_2O(CH_2CH_2O)xH$ where $Rf=F(CF_2CF_2)y$, x=0 to about 15 and y=1 to about 7; or an anionic phosphate fluorosurfactant of the following structure: $(RfCH_2CH_2O)xP(O)(ONH_4)y$ where $Rf=F(CF_2CF_2)z$, x=1 or 2, y=2 or 1 and z=1 to about 7, or mixtures thereof.

In another aspect of the invention there is provided an alcohol disinfecting composition, comprising;

a) ethanol present in an amount between about 60% to 70% percent v/v of the total composition;

b) a physiologically acceptable fluorosurfactant in an amount from about 0.01% to about 2.0% weight percent of the total composition;

c) at least one nonionic surfactant selected from the group consisting of polyethoxylated fatty alcohols present in an amount from about 0.01 to about 10.0% weight percent;

d) a foam stabilizing agent;

e) water in an amount to balance the total composition to 100% weight percent.

The present invention also provides an alcohol disinfecting composition comprising:

a) ethanol present in an amount between about 60% to 70% percent v/v of the total composition;

b) a physiologically acceptable anionic phosphate fluorosurfactant in an amount from about 0.01% to about 2.0% weight percent of the total composition;

c) at least 1% n-propanol;

d) foam stabilizing agents that at least include 1,3-Butyleneglycol % 2, Butoxyethanol in 0.001-3% ea;

e) a lipid layer enhancer such as a mixture of alkylglucoside and glyceryl oleate; and f) water in an amount to balance the total composition to 100% weight percent.

Gel-Like Compositions

In this aspect of the invention there is provided an alcohol gel-like composition, comprising;

a) an alcohol $C_{1-4}$, or mixtures thereof, present in an amount greater than about 40% percent v/v of the total composition;

b) at least one nonionic surfactant selected from the group consisting of a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, and mixtures thereof, present in an amount between about 0.10% to about 5% weight percent;

c) an emulsifier present in an amount between about 0.10% to about 3.0% weight percent; and d) water in an amount sufficient to form a stable gel-like disinfecting composition The compositions disclosed herein provide a wide variety and range of high alcohol content disinfecting products. According to the percentage of alcohol used in the compositions and by varying the proportions of the other constituents in the formulation, foams with differing properties can be achieved thereby allowing the production of foams that are either coarse or wet which quickly flatten, or foams that are soft which contain fine bubbles and which are relatively dry having long foam stability, or creamy thick foams that are gel-like. Also, the compositions may or may not be disinfecting according to the percentage of alcohol.

It was surprisingly found that by varying the percentages of the ingredients an alcohol gel-like composition was obtained which did not dry the hands or leave a sticky after-feel and that did not clog the gel dispensers, having the desired consistency and showing a viscosity of less than 4,000 cps.

Some of the compositions can conveniently be manufactured in a two step process such that most of the alcohol can be added at a later time and/or location making it the first part a desirable concentrate suitable for shipping less hazardous goods and weight. Warming the first part from 30 to 80 degrees Celsius, (depending on the particular composition) before adding the major portion of alcohol improves the long term stability of the compositions. This warming can either take place the same day in the same location where the finished composition is prepared or the concentrate first part can be stored or shipped elsewhere and the warming can take place either when the first part is mixing or right before adding the major portion of alcohol.

It should be evident that the described embodiment can be subjected to adjustment and/or improvement for specific applications either as a gel or a foam or to contain a desired active ingredient, without departing from the scope of the present invention. Different materials and/or ingredients will be then needed to compensate for the composition and/or foam stability disruption that might be generated by the change (i.e. introducing a more compatible secondary or even primary surfactant, adjusting the compatible foam stabilizer percentage and/or varying the relative amount of emulsifier and/or alcohol or water) or to compensate for shifts in desired viscosity and foam characteristics to obtained the desired gel (i.e. reduce the amount of fluorosurfactant or increase the polyethoxylated surfactants, or add an emulsifier and/or increase or decrease alcohol and/or water). These and other changes may be made in the details within the spirit of the invention, which is to be broadly construed and not to be limited except by the character of the claims appended hereto.

For example, the alcohol based compositions may contain up to 10% by weight of other active ingredients or additives or combinations thereof commonly added to aerosol compositions or to toiletries, cosmetics, pharmaceuticals, etc. Materials that may be added may include organic gums and colloids, lower alkanolamides of higher fatty acids, short chain diols and/or triols, alkylglucoside, fragrance, coloring matter, additional emollients, ultraviolet absorbers, solvents, emulsifiers, foam stabilizers or mixture of such stabilizers, suspending agents, buffers, conditioning agents, antioxidants, bactericides, medicinal active ingredient, and the like.

The present invention provides a composition, comprising;

a) an alcohol $C_{1-4}$, or mixtures thereof, present in an amount greater than about 40% v/v of the total composition;

b) at least one nonionic surfactant selected from the group consisting of a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, and mixtures thereof, present in an amount between about 0.10% to about 5% weight percent c) an emulsifier present in an amount between about 0.10% to about 3.0% weight percent; and d) water in an amount sufficient to form a stable gel-like composition with a viscosity less than 4,000 cps.

The invention will be described in connection with various specific examples, which are intended to be illustrative rather than limiting. Nevertheless, the present invention lends itself to the preparation of a wide variety of products, and it is to be understood that other embodiments may be utilized and that changes may be made without departing from the scope of the invention.

DETAILED DESCRIPTION OF THE INVENTION

Definitions

The term "emollient" as used herein refers broadly to materials which are capable of maintaining or improving the moisture level, compliance, or appearance of the skin when used repeatedly.

The term "emulsifier" as used herein refers to surfactants or other materials added in small quantities to a mixture of two miscible liquids for the purpose of aiding in the formation and stabilization of an emulsion.

The phrase "emulsifying ingredients" as used herein is synonymous with emulsifier defined above.

The term "emulsion" as used herein refers to a colloidal dispersion of one liquid in another.

The term "surfactant" as used herein is the widely employed contraction for "surface active agents" which is the descriptive generic term for materials that preferentially adsorb at interfaces as a result of the presence of both lyophilic and lyophobic structural units, the adsorption generally resulting in the alteration of the surface or interfacial properties of the system.

The term "fluorosurfactant" as used herein refers to a fluorinated surface active agent which enables the composition in which it is contained to clean, wet and foam.

The phrase "foam stabilizer" as used herein refers to an additive that increases the amount or persistence of foam produced by a surfactant system.

The phrase "gel-like composition" as used herein refers to a hydroalcoholic solution with at least 40% v/v alcohol content, which is thickened by the use of emulsifiers and surfactant to have a viscosity greater than water and less than 4,000 cps.

The term "disinfect" as used herein means to destroy or reduce harmful microorganisms.

The present invention provides compositions with high contents of lower alcohol ($C_{1-4}$) able to be dispensed as a gel or a foam. The foamable compositions when mixed with air deliver a stable foam to provide an alcoholic liquid solution which can be used for personal cleaning or for disinfecting purposes and which breaks on pressure application such as when a user rubs their hands or when applied over a surface. The gel composition delivers a liquid of the appropriate consistency to be readily spread on the hands, yet without dripping off. This gel composition with at least 60% v/v alcohol provides an effective disinfectant that does not leave a tacky after-feel once the alcohol has evaporated and that is common to such alcohol gels which use thickeners and gelling agents that have been used commonly in the past during single or multiple applications. The gel composition does not easily clog the dispensers as common gel products do.

The alcohol used in the present invention is a lower hydrocarbon chain alcohol such as a $C_{1-4}$ alcohol. The preferred alcohol is chosen from ethanol, 2-propanol, or n-propanol, most preferably ethanol, well accepted by Health Care personnel as an adequate disinfectant at the right percentages. The invention anticipates that a single alcohol may be used or that a blend of two or more alcohols may comprise the alcohol content of the composition either for a gel-like or foamable product.

Foamable Compositions

One of the main achievements of the present invention is making compositions with a greater than 40% v/v alcohol content able to be dispensed as a cosmetically appealing foam. The other important achievement is to obtain an alcohol gel without using the typical gelling agents know to those skilled in the art which would not clog dispensers or leave a tacky after-feel.

The use of a fluorosurfactant is the key ingredient as the primary foaming agent in the compositions designed to foam disclosed herein. Fluorosurfactants have various interesting properties such as leaving little residue, being able to function in harsh chemical and thermal environments; they have an unparalleled wetting power, etc. Unlike traditional surfactants, they show unusual surface-active properties in organic solvents that are known to those skilled in the art, and that have made them widely used for applications in coatings, oilfield, material finishes, cleaning, paints, etc.

The fluorosurfactants suitable for these types of compositions may include, but are not limited to, ethoxylates, glycerol esters, amine oxides, acetylenic alcohol derivatives, carboxylates, phosphates, carbohydrate derivatives, sulfonates, betaines, esters, polyamides, silicones, and hydrocarbon surfactants that have been fluorinated and are compatible with the other components being used for a particular formulation.

A preferred fluorosurfactant is polytetrafluoroethylene acetoxypropyl betaine $CF_3CF_2(CF_2CF_2)nCH_2CH_2(OAc)CH_2N+(CH_3)_2CH_2COO-$, where n=2-4. However, it is contemplated that other fluorosurfactants may be used including as non-limiting examples for use in the present invention an ethoxylated nonionic fluorosurfactant of the following structure: $RfCH_2CH_2O(CH_2CH_2O)_xH$ where $Rf=F(CF_2CF_2)y$, x=0 to about 15 and y=1 to about 7; an anionic phosphate fluorosurfactant of the following structure: $(RfCH_2CH_2O)_x P(O)(ONH_4)_y$, where $Rf=F(CF_2CF_2)z$, x=1 or 2, y=2 or 1, x+y=3, and z=1 to about 7 or mixtures thereof.

It was surprisingly found that despite the characteristics of fluorosurfactants, there was little or no information on their use to produce a foamable product with high alcohol content other than the one using non-ionic fluorosurfactants and pressurized gas as a foamer as taught in U.S. Pat. No. 4,440,653 incorporated herein by reference.

Furthermore, in order to obtain a high alcohol content product able to produce a foam even if no pressurized containers or propellants are used would require surface tension values as low as possible so that the pressure required to produce such foam by hand pumps and mechanical means would be sufficient. Hence, the lower than 20 dynes/cm (0.01% DW 25° C.) surface tension values achievable with these surfactants made them suitable for the application.

During the development of the present invention, it was unexpectedly found that a quick breaking aerated foam could even be obtained when using just ethanol and the fluorosurfactant, while using traditional surfactants at even double the percentage bore results that could not be even slightly similar and no foam at all could be obtained.

In order to achieve a commercially suitable formulation, reducing the amount of fluorosurfactant used while using the assistance of other ingredients such as secondary surfactants, emulsifiers, foam stabilizers, fragrances, and the like ingredients employed in cosmetics, aerosols, toiletries, personal care, etc. is one of the approaches followed. One of the commercial products obtained uses emulsifiers and polyethoxylated fatty acid surfactants disclosed in U.S. Pat. Nos. 5,167,950 and 6,090,395, both incorporated herein by reference, while other examples use a combination of different foam stabilizers to achieve a similar result.

Examples of secondary surfactants that may be used in the present compositions include alkylglucosides, a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, a betaine, a sulfobetaines, imidazoline derivatives, aminoacid derivatives, lecithins, phosphatides, some amine oxides and sulfoxides and mixtures thereof, present in an amount between about 0.10% to about 5% weight percent.

A preferred betaine is cocamidopropyl betaine. A preferred alkylglucoside is cocoglucoside. Preferred polyethoxylated fatty alcohols are polyethoxylated stearyl alcohol (21 moles ethylene oxide) and polyethoxylated stearyl alcohol (2 moles ethylene oxide), and a combination of these two.

The compositions may include an antimicrobial agent. The following antimicrobials are offered as non-limiting examples of suitable antimicrobials for use in the present invention and may include chlorhexidine salt, iodine, a complexed form of iodine, parachlorometaxylenol, triclosan, hexachlorophene, a phenol, a surfactant having a long chain hydrophobic group and a quaternary group, hydrogen peroxide, silver, a silver salt, silver oxide, and mixtures thereof.

A preferred antimicrobial agent in the present compositions is chlorhexidine gluconate (CHG) present in an amount between about 0.50% to about 4.0% weight percent. Another preferred antimicrobial agent is didecyl dimethyl diamonium chloride in an amount between about 0.05% to 5% weight percent.

If the amount of ingredients employed is little enough not to leave a tacky feeling after the composition evaporates after single or multiple uses, and this is achieved while maintaining at least 60% v/v ethanol or n-propanol concentration or 70% v/v isopropanol, then the composition would be ideal for use as an alcohol hand sanitizer/disinfectant foamable composition.

The addition of water to the alcohol produces a more stable foam while allowing to reduce the amount of fluorosurfactant required to foam the product. For instance, using 0.5 to 1.0% fluorosurfactant with a 50 to 60% v/v alcohol water solution produces a stable foam that does not readily collapse and that produces a stable puff that does not fall even when inverted and does not collapse until pressure is applied (such as when rubbed in hands or on over a surface) to provide an alcoholic liquid solution.

The use of a mild non-irritant surfactant widely used in the cosmetic industry such as cocamidopropyl betaine as a secondary surfactant is more suitable to prepare the foamable hydroalcoholic composition of the present invention depending on the fluorosurfactant being used.

In order to stabilize the foam, foam stabilizers, as well as emulsifying ingredients have been tried with good results in allowing the product to be dispensed as a foam even when no propellant and/or pressurized container systems are used.

Examples of compatible foam stabilizers that can optionally be employed include lactic acid esters of monoglycerides, cationic emulsifiers, triquaternized stearic phospholipid complex, hydroxystearamide propyltriamine salts, lactic acid monoglycerides, food emulsifiers such as glyceryl monostearate, propylene glycol monostearate, sodium stearoyl lactylate, silicone wax, an encapsulated oil, Microcapsule Mineral Oil.

A preferred foam stabilizer used in the present foamable compositions is cetyl betaine. A preferred combination of foam stabilizers is that of butyleneglycol, butoxyethanol and n-propanol.

Examples of moisturizers and/or emollients which may be used in the present formulations include lanolin, vinyl alcohol, polyvinyl pyrrolidone and polyols selected from the group consisting of glycerol, propylene glycol, glyceryl oleate and sorbitol, cocoglucoside or a fatty alcohol selected from the group consisting of cetyl alcohol, stearyl alcohol, lauryl alcohol, myristyl alcohol and palmityl alcohol, cetyl alcohol, ceteareth 20, and combinations thereof, present in an amount up to about 5%.

The compositions formulated to be dispensed as a foam may be stored in an unpressurized dispenser having a dispenser pump for mixing the composition with air and dispensing foam therefrom. The composition may include an aerosol propellant in an amount from about 3 to about 20 weight percent of the total composition for pressurized discharge of the foam. The aerosol propellant may include propane, carbon dioxide, butane, dichloro difluoro methane, dichloro tetra fluoro ethane, octafluorocyclo butane; 1,1,1,2-tetrafluoroethane; 1,1,1,2,3,3,3 heptafluoropropane, and 1,1,1,3,3,3, -hexafluoropropane. When stored in a metal container with propellant, the formulation may include a corrosion inhibitor such as sorbic acid, benzoic acid, potassium sorbate and sodium benzoate, in an amount from about 0.1 to about 5 weight percent of the total composition.

Gel-Like Compositions

Some of compositions studied had some gel-like properties. This characteristic led to the second most important achievement of the present invention; that is an alcohol gel with viscosities less than 4,000 cps that do not use the conventional polymeric thickeners (i,e, cellulose derivatives, carbomers, etc) that are known to leave a sticky residue on surfaces on single and multiple applications that builds up. This discourages users and tends to clog the dispensers.

In order to prepare a gel-like composition, a fluorosurfactant is not required to form the gel, however, using a small amount improves the after-feel, it also allows one to reduce the usage of other surfactants required, therefore improving the performance of the composition. The use of the fluorosurfactant also noticeably improves the spreadability of the gel disenfecting compositions on the hands or a surface.

The following is a basic formulation of the gel-like compositions. An alcohol $C_{1-4}$, or mixtures thereof, present in an amount greater than about 40% v/v of the total composition, one or more nonionic surfactants present in an amount between about 0.10% to about 5% weight percent, an emulsifier present in an amount between about 0.10% to about 3.0% weight percent, and water in an amount sufficient to form a stable gel-like composition.

Non-limiting examples of non-ionic surfactants include poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, and mixtures thereof.

A preferred non-ionic surfactant includes polyethoxylated fatty alcohols such as polyethoxylated stearyl alcohol (21 moles ethylene oxide) and polyethoxylated stearyl alcohol (2 moles ethylene oxide), and/or a combination of polyethoxylated fatty alcohols.

To make the gel-like compositions for personal hygiene applications, the compositions may include a physiologically acceptable fluorinated surface active agent up to about 2.5%. A preferred fluorinated surface active agent is that used in the gel-like compositions, namely polytetrafluoroethylene acetoxypropyl betaine $CF_3CF_2(CF_2CF_2)nCH_2CH_2(OAc)CH_2N+(CH_3)_2CH_2COO—$, where n=2-4.

Another fluorinated surface active agent also preferred is an ethoxylated nonionic fluorosurfactant of the following structure: $RfCH_2CH_2O(CH_2CH_2O)_xH$ where $Rf=F(CF_2CF_2)y$, x=0 to about 15 and y=1 to about 7 and yet another one is an anionic phosphate fluorosurfactant of the following structure: $(RfCH_2CH_2O)_xP(O)(ONH_4)_y$ where $Rf=F(CF_2CF_2)z$, x=1 or 2, y=2 or 1, x+y=3, and z=1 to about 7 or mixtures thereof.

The following non-limiting examples are set forth to show for the various preferred embodiments and are not in any way to limit the scope of the present invention.

EXAMPLES

Examples 1 through 12 were prepared to illustrate the ability to produce alcohol-based formulations which can be dispensed as foams using different surfactants and a solution of water and 50% ethanol. Examples 13 through 18 show increasing concentrations of ethanol and fluorosurfactant to produce foam. Examples 19 through 30 illustrate the ability to produce foam using different surfactants and a solution of 70% v/v Isopropanol. All parts and percentages are expressed by weight unless otherwise indicated.

| Ingredients | Amount Ex. 1 | Ex. 2 | Ex. 3 | Ex. 4 | Ex. 5 | Ex. 6 |
|---|---|---|---|---|---|---|
| S.D. Alcohol 3-A | 50.00 | 50.00 | 50.00 | 50.00 | 50.00 | 50.00 |
| Fluorosurfactant | 0.50 | — | — | — | — | — |
| Cocamidopropyl betaine (1) | — | 8.00 | — | — | — | — |
| Alkylglucoside (2) | — | — | 8.00 | — | — | — |
| Alkylglucoside (3) | — | — | — | 8.00 | — | — |
| Glycomul L | — | — | — | — | 8.00 | — |
| Sorbitan Sesquioleate | — | — | — | — | — | 8.00 |
| Deionized Water | 49.50 | 42.00 | 42.00 | 42.00 | 42.00 | 42.00 |
| Total % | 100.00 | 100.00 | 100.00 | 100.00 | 100.00 | 100.00 |

(1) Amphoteric,
(2) Nonionic,
(3) Anionic

| Ingredients | Amount Ex. 7 | Ex. 8 | Ex. 9 | Ex. 10 | Ex. 11 | Ex. 12 |
|---|---|---|---|---|---|---|
| S.D. Alcohol 3-A | 50.00 | 50.00 | 50.00 | 50.00 | 50.00 | 50.00 |
| Polysorbate 20 | 8.00 | — | — | — | — | — |
| Polyoxyethylene Sorbitan Monooleate | — | 8.00 | — | — | — | — |
| Sorbitan Monooleate | — | — | 8.00 | — | — | — |
| Cocamidopropyl betaine & sodium caproyl lactate | — | — | — | 8.00 | — | — |
| Cocamidopropyl hydroxysultaine | — | — | — | — | 8.00 | — |
| Sodium Cocoamphoacetate | — | — | — | — | — | 8.00 |
| Deionized Water | 42.00 | 42.00 | 42.00 | 42.00 | 42.00 | 42.00 |
| Total % | 100.00 | 100.00 | 100.00 | 100.00 | 100.00 | 100.00 |

| Ingredients | Amount Ex. 13 | Ex. 14 | Ex. 15 | Ex. 16 | Ex. 17 | Ex. 18 |
|---|---|---|---|---|---|---|
| S.D. Alcohol 3-A | 50.00 | 60.00 | 65.00 | 70.00 | 80.00 | 92.50 |
| Fluorosurfactant | 0.10 | 0.75 | 0.80 | 1.50 | 2.00 | 7.5 |
| Deionized Water | 49.90 | 39.25 | 34.20 | 28.50 | 18.00 | — |
| Total % | 100.00 | 100.00 | 100.00 | 100.00 | 100.00 | 100.00 |

| Ingredients | Amount Ex. 19 | Ex. 20 | Ex. 21 | Ex. 22 | Ex. 23 | Ex. 24 |
|---|---|---|---|---|---|---|
| 70% v/v Isopropanol | 99.90 | 92.00 | 92.00 | 92.00 | 92.00 | 92.00 |
| Fluorosurfactant | 0.10 | — | — | — | — | — |
| Cocamidopropyl betaine (1) | — | 8.00 | — | — | — | — |
| Alkylglucoside (2) | — | — | 8.00 | — | — | — |
| Alkylglucoside (3) | — | — | — | 8.00 | — | — |
| Glycomul L | — | — | — | — | 8.00 | — |
| Sorbitan Sesquioleate | — | — | — | — | — | 8.00 |
| Total % | 100.00 | 100.00 | 100.00 | 100.00 | 100.00 | 100.00 |

(1) Amphoteric,
(2) Nonionic,
(3) Anionic

| Ingredients | Amount Ex. 25 | Ex. 26 | Ex. 27 | Ex. 28 | Ex. 29 | Ex. 30 |
|---|---|---|---|---|---|---|
| 70% v/v Isopropanol | 92.00 | 92.00 | 92.00 | 92.00 | 92.00 | 92.00 |
| Polysorbate 20 | 8.00 | — | — | — | — | — |
| Polyoxyethylene Sorbitan Monooleate | — | 8.00 | — | — | — | — |
| Sorbitan Monooleate | — | — | 8.00 | — | — | — |

-continued

| Amount Ingredients | Ex. 25 | Ex. 26 | Ex. 27 | Ex. 28 | Ex. 29 | Ex. 30 |
|---|---|---|---|---|---|---|
| Cocamidopropylbetaine & sodium caproyl lactate | — | — | — | 8.00 | — | — |
| Cocamidopropyl hydroxysultaine | — | — | — | — | 8.00 | — |
| Sodium Cocoamphoacetate | — | — | — | — | — | 8.00 |
| Total % | 100.00 | 100.00 | 100.00 | 100.00 | 100.00 | 100.00 |

The solutions prepared, were evaluated as to whether foam was produced or not and if so, then the foam produced was described as follows:

| Example | Foam Produced | Foam Evaluation/Description/Characteristics |
|---|---|---|
| Ex. 1 | Yes | Very good stable stiff puff creamy and soft lasts minutes |
| Ex. 2 | No | Just Very Wet Bubbles produced lasting <10 seconds |
| Ex. 3 | No | — |
| Ex. 4 | No | — |
| Ex. 5 | No | — |
| Ex. 6 | No | Just Very Wet Bubbles produced lasting <7 seconds |
| Ex. 7 | No | Just Very Wet Bubbles produced lasting <10 seconds |
| Ex. 8 | No | — |
| Ex. 9 | No | Just Very Wet Bubbles produced lasting <10 seconds |
| Ex. 10 | No | — |
| Ex. 11 | No | — |
| Ex. 12 | No | — |
| Ex. 13 | Yes | Very good stable stiff puff creamy and soft lasts minutes |
| Ex. 14 | Yes | Very good creamy and soft lasts more than a minute |
| Ex. 15 | Yes | Very good creamy and soft lasts more than a minute |
| Ex. 16 | Yes | Very good creamy and soft lasts more than a minute |
| Ex. 17 | Yes | Quick fast breaking foam lasts more than a 15 secs |
| Ex. 18 | Yes | Quick fast breaking foam lasts more than a 10 secs |
| Ex. 19 | Yes | Quick fast breaking foam lasts more than a 20 secs |
| Ex. 20 | No | — |
| Ex. 21 | No | — |
| Ex. 22 | No | — |
| Ex. 23 | No | — |
| Ex. 24 | No | — |
| Ex. 25 | No | — |
| Ex. 26 | No | — |
| Ex. 27 | No | — |
| Ex. 28 | No | — |
| Ex. 29 | No | — |
| Ex. 30 | No | — |

Comparatively, it was also found that for instance, Cocamidopropyl betaine (CAPB) alone even at 40% ethanol and at 3% CAPB, was unable to produce as good results as those with 60% v/v ethanol, and fluorosurfactants using much less percentage (less than 1.0%). Cocamidopropyl betaine does not give any acceptable foam above that percentage of alcohol and the lower than 60% v/v alcohol content makes it inadequate for a sanitizing solution. Also the solution left an unacceptable feeling on the skin after the alcohol evaporated (i.e. a soapy sticky feeling) indicating high levels of surfactant.

Very interestingly fluorosurfactants seemed to be a likely way to achieve a foaming composition that contains more than 40% v/v alcohol. The fact that foam could be achieved even when no added water or ingredients are used other than 95% v/v alcohol and the fluorosurfactant as shown in example 18 makes the present invention suitable for many different applications.

Below are some specific examples for compositions following the above formulation to produce alcohol hand sanitizing solutions; more than one being a foamable composition with alcohol being the only disinfectant ingredient, while other foamable compositions use an added antimicrobial such as Chlorhexidine Digluconate or Didecyl Dimethyl Diammonium Chloride and the third group being alcohol gel-like hand sanitizing solutions.

Example 31

Alcohol Hand Sanitizing Foamable Disinfecting Composition 0.01-1.0% * amphoteric, anionic or non-ionic fluorosurfactant (primary surfactant)

0.01-1.0% cocoamidopropylbetaine (secondary surfactant)

0.05-1.0% cetyl betaine (foam stabilizing agent)

0.10-1.5% emulsifier fatty alcohol ROH 16-22 carbons or combination that works well in a final formulation containing 60-70% v/v ethanol Q.S. water Preferably Polytetrafluoroethylene Acetoxypropyl Betaine $CF_3CF_2(CF_2CF_2)_nCH_2CH_2(OAc)CH_2N^+(CH_3)_2CH_2COO^-$, where n=2-4 or an ethoxylated nonionic fluorosurfactant of the following structure: $RfCH_2CH_2O(CH_2CH_2O)_xH$ where $Rf=F(CF_2CF_2)y$, x=0 to about 15 and y=1 to about 7; or an anionic phosphate fluorosurfactant of the following structure: $(RfCH_2CH_2O)_xP(O)(ONH_4)_y$, where $Rf=F(CF_2CF_2)z$, x=1 or 2, y=2 or 1, x+y=3, and z=1 to about 7, or mixtures thereof.

Example 32

Alcohol Hand Sanitizing Foamable Disinfecting Composition Concentrate
0.01-1.0% * amphoteric, anionic or non-ionic fluorosurfactant (primary surfactant)
0.01-12.0% 1,3 Butyleneglycol, 2-Butoxyethanol, n-propanol (foam stabilizing agents)
0.05-5.0% cocoglucoside, glycerin, glyceryl oleate (moisturizers, emollients and the like)
60-70% v/v ethanol, n-propanol, isopropanol or a combination thereof.
Q.S. water
  Preferably an anionic phosphate fluorosurfactant of the following structure: $(RfCH_2CH_2O)_xP(O)(ONH_4)_y$, where $Rf=F(CF_2CF_2)z$, $x=1$ or $2$, $y=2$ or $1$, $x+y=3$, and $z=1$ to about 7 or an ethoxylated nonionic fluorosurfactant of the following structure: $RfCH_2CH_2O(CH_2CH_2O)_xH$ where $Rf=F(CF_2CF_2)y$, $x=0$ to about 15 and $y=1$ to about 7; or Polytetrafluoroethylene Acetoxypropyl Betaine $CF_3CF_2(CF_2CF_2)_nCH_2CH_2(OAc)CH_2N^+(CH_3)_2CH_2COO^-$, where $n=2-4$, or mixtures thereof.

Example 33

Alcohol Hand Sanitizing Foamable Disinfecting Composition
  a) ethanol present in an amount between about 60% to 70% percent v/v of the total composition;
  b) a physiologically acceptable anionic phosphate fluorosurfactant in an amount from about 0.01% to about 2.0% weight percent of the total composition;
  c) at least 1% n-propanol
  d) foam stabilizing agents that at least include 1,3-Butyleneglycol % 2, Butoxyethanol in 0.001-3% ea.
  e) a lipid layer enhancer such as a mixture of alkylglucoside and glyceryl oleate
  f) water in an amount to balance the total composition to 100% weight percent.

Example 34

Chlorhexidine Gluconate (CHG) & Alcohol Hand Sanitizing Foamable Disinfecting Composition
Formulations 31 or 32 added with
0.50-4.0% Chlorhexidine Gluconate (CHG)

Example 35

Formulations 31 or 32 added with
0.01-5.0% Didecyl Dimethyl Diammonium Chloride

Example 36

Alcohol Hand Sanitizing Gel-Like Disinfecting Composition with a Viscosity Less than 4,000 cps
0.0-1.0% * amphoteric, anionic or non-ionic fluorosurfactant (primary surfactant)
0.10-2.0% an emulsifier moisturizer and/or emollient preferably a non-ionic surfactant and/or a combination of cetearyl alcohol and ceteareth 20 or a combination thereof to give a composition with a viscosity of less than 4,000 cps;
0.50-4.0% a combination of nonionic surfactants specifically from the group of the polyethoxylated fatty alcohols
60-70% v/v ethanol
Q.S. water
  Preferably Polytetrafluoroethylene Acetoxypropyl Betaine $CF_3CF_2(CF_2CF_2)_nCH_2CH_2(OAc)CH_2N^+(CH_3)_2CH_2COO^-$, where $n=2-4$ or an ethoxylated nonionic fluorosurfactant of the following structure: $RfCH_2CH_2O(CH_2CH_2O)_xH$ where $Rf=F(CF_2CF_2)y$, $x=0$ to about 15 and $y=1$ to about 7; or an anionic phosphate fluorosurfactant of the following structure: $(RfCH_2CH_2O)_xP(O)(ONH_4)_y$, where $Rf=F(CF_2CF_2)z$, $x=1$ or $2$, $y=2$ or $1$, $x+y=3$, and $z=1$ to about 7, or mixtures thereof.

The process to prepare the compositions of the present invention described herein is straightforward since most of the ingredients are liquid. When wax type ingredients are to be used, they can be incorporated by warming up to 40-45° C. preferably to the alcohol portion while mixing and then allowing it to cool down or they could be added in "cold", at room temperature to the alcohol before any other ingredient and mixed until completely incorporated before adding the rest of the ingredients according to the composition. Whether all ingredients are liquid or not, warming from 30 to 80 degrees Celsius, (depending on the particular composition) increases the long term stability of the compositions. Active ingredients could be pre-dissolved into the water first. A process that anyone knowledgeable enough of the art would have no problem implementing. If a specific formulation cannot be adjusted for the foamable composition in the percentages of the ingredients, then there is still the option of modifying the characteristics of the foaming pump, such as changing pressures, screen sizes, etc.

The compositions described within the present invention improve over prior similar products commercially available in the high concentrations of alcohol, as well as in the fact of being able to foam even with no propellants or pressurized containers (using propellants would improve considerably the quality of the foam) and being able to produce alcohol gel-like compositions that do not leave a sticky after-feel that builds up and do not clog the dispensers after single or multiple applications.

Depending on the alcohol concentration and the application of the particular composition the foam produced can widely vary, being at the high end of a relatively fast breaking variety stable enough to be thoroughly spread onto the skin without waste in a unique way and the gel-like composition viscosity varies with the alcohol concentration. The gel-like composition obtained is a unique approach that does not follow the traditional ways of making alcohol gels. In summary it could be said that the stated invention has exceeded expectations.

Due to the nature of the base composition with respect to the alcohol concentration and the quality of the ingredients, one of the logical first applications for the present invention would be as an alcohol hand disinfectant composition either for a foamable product or an alcohol gel-like product, examples of which are described above. Nevertheless, the present invention lends itself to the preparation of a wide variety of products, and it is to be understood that other embodiments may be utilized and that changes may be made without departing from the scope of the invention.

Consequently, it is intended that the claims be interpreted to cover such modifications and equivalents. To note a few, the following may be mentioned: medicated foams and gels, sunscreen foams and gels, hand cream foams, brush-less shaving cream foams, shower or bath oil foams, dry hair shampoo foams, make-up remover foams, analgesic foam rubs and gels, hair grooming foams and antiperspirants hair cleaning foam, antiperspirant foam, hair conditioner foams.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

References Cited
U.S. PATENT DOCUMENTS

| | | | |
|---|---|---|---|
| 2,054,989 | September 1936 | Moore | 167/58 |
| 3,131,153 | April 1964 | Klausner | 252/305 |
| 3,962,150 | June 1976 | Leonard et al | 252/542 |
| 4,440,653 | April 1984 | James et al | 252/8.55 |
| 5,167,950 | December 1992 | Lins | 424/47 |
| 4,956,170 | September 1990 | Lee | 514/772.1 |
| 5,629,006 | May 1997 | Minh et al | 424/405 |
| 5,906,808 | May 1999 | Osborne, et al | 424/43 |
| 5,928,993 | July 1999 | Ingegärd | 504/116 |
| 5,951,993 | September 1999 | Scholz et al | 424/405 |
| 6,090,395 | July 2000 | Asmus et al | 424/401 |
| 6,610,315 | August 2003 | Scholz et al | 424/415 |
| 6,623,744 | September 2003 | Asmus et al | 424/401 |
| 6,562,360 | May 2003 | Scholz et al | 424/405 |

Other Publications

Myers, Drew; "Surfactant Science and Technology", second edition, Drew Myers, VCH Publishers, New York, 1992
Reduce Tension Dupont Zonyl® Fluorosurfactants Field Manual published by Dupont Co on May 2001.

What is claimed is:

1. A composition, comprising:
 a) an alcohol $C_{1-4}$, or mixtures thereof, present in an amount greater than or equal to about 60% v/v of the total composition;
 b) an effective fluorinated surface active agent for wetting and foaming present in an amount of at least 0.001% by weight of the total composition wherein the fluorinated surface active agent is selected from the group consisting of fluorinated glycerol esters, amine oxides, acetylenic alcohol derivatives, carboxylates, phosphates, carbohydrate derivatives, sulfonates, betaines, esters, polyamides, and hydrocarbon surfactants; and
 c) water present in an amount to balance the total composition to 100% by weight.

2. The composition according to claim 1 wherein the effective fluorinated surface active agent is an anionic phosphate fluorosurfactant.

3. The composition according to claim 1 further including at least one additional surfactant for adjusting properties of the composition and/or the resulting foam produced from the composition.

4. The composition according to claim 3 wherein the additional surfactant is selected from the group consisting of a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, an alkylglucoside, a betaine, a sulfobetaine, an imidazoline derivative, an aminoacid derivative, a lecithin, a phosphatide, an amine oxide, a sulfoxide and mixtures thereof, present in an amount between about 0.10% to about 5% by weight.

5. The composition according to claim 4 wherein the additional surfactant is a betaine.

6. The composition according to claim 4 wherein the additional surfactant is an alkylglucoside.

7. The composition according to claim 1 including a foam stabilizing agent present in an amount up to 5% by weight.

8. The composition according to claim 1 including any one of a moisturizer, emollient and combinations thereof selected from the group consisting of
 lanolin,
 vinyl alcohol,
 polyvinyl pyrrolidone,
 polyols,
 a fatty alcohol,
 ceteareth 20,
 an alkylglucoside,
 and combinations thereof, present in an to 5% by weight.

9. The composition according to claim 1 including an antimicrobial agent.

10. The composition according to claim 1 further comprising constituents selected from the group consisting of
 organic gums and colloids,
 lower alkanolamides of higher fatty acids,
 short chain diols and/or triols.
 fragrance,
 coloring matter,
 ultraviolet absorbers,
 solvents,
 suspending agents,
 buffers,
 conditioning agents,
 antioxidants,
 bactericides and
 medicinally active ingredients,
 and combinations thereof.

11. The composition of claim 1, wherein:
 a) the alcohol $C_{1-4}$, or mixtures thereof, is present in an amount between about 60% to about 80% v/v of the total composition;
 b) the effective fluorinated surface active agent is present in an amount from about 0.01% to about 2.0% by weight of the total composition;
 and further comprising
 c) a foam stabilizing agent present in an amount from about 0.01 to about 12.0% by weight; and
 d) any one of moisturizers, emollients and combinations thereof present in an amount from about 0.05 to about 5.0% by weight.

12. A method of forming a skin disinfecting foam containing alcohol, comprising the steps of:
 activating a dispenser pump of an unpressurized dispenser to combine an alcohol-fluorosurfactant mixture with air to form and dispense a skin disinfecting foam containing alcohol, wherein the alcohol-fluorosurfactant mixture comprises an alcohol $C_{1-4}$, or mixtures thereof, present in an amount greater than or equal to about 60% v/v of the total composition, a physiologically acceptable effective fluorinated surface active agent for foaming present in an amount of at least 0.001% by weight of the total composition, and water present in an amount to balance the total composition to 100% by weight;
wherein the effective physiologically acceptable fluorinated surface active agent is selected from the group consisting of fluorinated glycerol esters, amine oxides, acetylenic alcohol derivatives, carboxylates, phosphates, carbohydrate derivatives, sulfonates, betaines, esters, polyamides, hydrocarbon surfactants, and combinations thereof.

13. The method according to claim 12 further including at least one additional surfactant for adjusting properties of the foam produced from the composition.

14. The method according to claim 13 wherein the additional surfactant is selected from the group consisting of a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, an alkylglucoside, a betaine, a sulfobetaine, an imidazoline derivative, an aminoacid derivative, a lecithin, a phosphatide, an amine oxide, a sulfoxide and mixtures thereof, present in an amount between about 0.10% to about 5% by weight.

15. The method according to claim 12 wherein the effective physiologically acceptable fluorinated surface active agent is a fluorosurfactant present in an amount from about 0.1% to about 10.0% by weight of the total composition.

16. The method according to claim 12 wherein the alcohol is ethanol, propanol or a mixture thereof.

17. A method for personal disinfecting comprising:
applying to a person's skin a skin-disinfecting alcohol foam composition which comprises
a) air mixed under low pressure with
b) a liquid comprising
i) an alcohol $C_{1-4}$, or mixtures thereof, present in an amount greater than or equal to about 60% v/v of the total composition;
ii) water present in an amount to balance the total composition to 100% by weight; and
iii) a physiologically acceptable effective fluorinated surface active agent for foaming present in an amount of at least 0.001% by weight of the total composition,
wherein the effective physiologically acceptable fluorinated surface active agent is selected from the group consisting of fluorinated glycerol esters, amine oxides, acetylenic alcohol derivatives, carboxylates, phosphates, carbohydrate derivatives, sulfonates, betaines, esters, polyamides, hydrocarbon surfactants and combinations thereof.

18. The method according to claim 17 wherein the alcohol foam composition further includes at least one additional surfactant for adjusting properties of the composition and/or the resulting foam produced from the composition.

19. The method according to claim 18 wherein the additional surfactant is selected from the group consisting of a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, an alkylglucoside, a betaine, a sulfobetaine, an imidazoline derivative, an aminoacid derivative, a lecithin, a phosphatide, an amine oxide, a sulfoxide and mixtures thereof, present in an amount between about 0.10% to about 5% by weight.

20. The method according to claim 17 wherein the alcohol foam composition includes a foam stabilizing agent present in an amount up to 5% by weight.

* * * * *